(12) United States Patent
Brammer et al.

(10) Patent No.: US 10,077,281 B2
(45) Date of Patent: Sep. 18, 2018

(54) CRYSTALLINE LIGAND

(71) Applicant: Dow Technology Investments LLC, Midland, MI (US)

(72) Inventors: Michael A. Brammer, Freeport, TX (US); Glenn A. Miller, South Charleston, WV (US); Marinus A. Bigi, Freeport, TX (US); George R. Phillips, South Charleston, WV (US); Britt A. Vanchura, II, Midland, MI (US); Kenneth L. Kearns, Jr., Midland, MI (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/564,338

(22) PCT Filed: Jun. 15, 2016

(86) PCT No.: PCT/US2016/037474
§ 371 (c)(1),
(2) Date: Oct. 4, 2017

(87) PCT Pub. No.: WO2016/205264
PCT Pub. Date: Dec. 22, 2016

(65) Prior Publication Data
US 2018/0141968 A1  May 24, 2018

Related U.S. Application Data

(60) Provisional application No. 62/182,017, filed on Jun. 19, 2015.

(51) Int. Cl.
| C07F 9/6574 | (2006.01) |
|---|---|
| B01J 35/02 | (2006.01) |
| B01J 31/24 | (2006.01) |

(52) U.S. Cl.
CPC ....... *C07F 9/65746* (2013.01); *B01J 31/2419* (2013.01); *B01J 35/02* (2013.01)

(58) Field of Classification Search
CPC .................................................. C07F 9/65746
See application file for complete search history.

(56) References Cited

U.S. PATENT DOCUMENTS

| 4,769,498 A | 9/1988 | Billig et al. |
| 5,312,996 A | 5/1994 | Packett |
| 8,796,481 B2 | 8/2014 | Berens et al. |
| 2013/0225849 A1 | 8/2013 | Berens et al. |
| 2014/0288322 A1 | 9/2014 | Miller et al. |

FOREIGN PATENT DOCUMENTS

| CN | 1986055 A | 6/2007 |
| CN | 101684130 A | 3/2010 |
| CN | 102432638 A | 5/2012 |
| WO | 2013/098370 A1 | 7/2013 |
| WO | 2015/175158 A1 | 11/2015 |

OTHER PUBLICATIONS

Yuan, H., et al. "Crystal structure of 6,6'-(3,3',5,5'-Tetra-tertbutylbiphenyl-2,2'-diyl)bis)oxy)didibenzo-[d,f]-[1,3,2,]dioxaphosphepine", Chinese Journal of Structural Chemistry, vol. 31 (5), p. 673, May 2012.
Annemiek Van Rooy et al: "Bulky Diphosphite-Modified Rhodium Catalysts: Hydroformylation and Characterization", Organimetallics, American Chemical Society, US, vol. 15, Feb. 23, 1996, pp. 835-847, XP007911079.
PCT/US2016/037474, International Search Report and Written Opinion dated Jul. 29, 2016.
PCT/US2016/037474, International Preliminary Report on Patentability dated Dec. 19, 2017.

*Primary Examiner* — Joseph R Kosack

(57) ABSTRACT

A ligand crystal structure of 6,6'-[[3,3',5,5'-tetrakis(1,1-dimethylethyl)-[1,1'-biphenyl]-2,2'-diyl]bis(oxy)]bisdibenzo[d,f][1,3,2]-dioxaphosphepin. Formule (I)

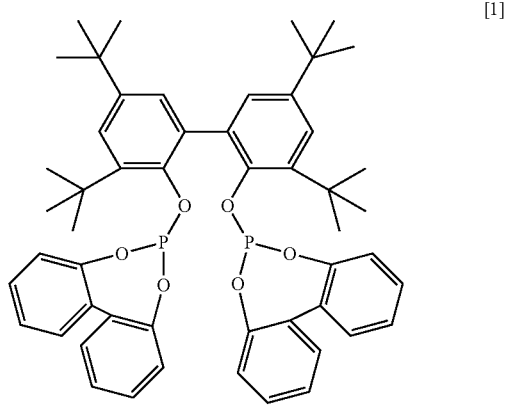

8 Claims, 4 Drawing Sheets

CRYSTALLINE LIGAND

BACKGROUND OF THE INVENTION

The invention relates to a crystalline form of a bisphosphite ligand.

Bisphosphites are commonly used as ligands for transition-metal catalyzed reactions such as hydroformylation and hydrocyanation. One commonly used bisphosphite ligand is 6,6'-[[3,3',5,5'-tetrakis(1,1-dimethylethyl)-[1,1'-biphenyl]-2,2'-diyl]bis(oxy)]bisdibenzo[d,f][1,3,2]-dioxaphosphepin, (hereinafter Ligand A), shown in Formula 1:

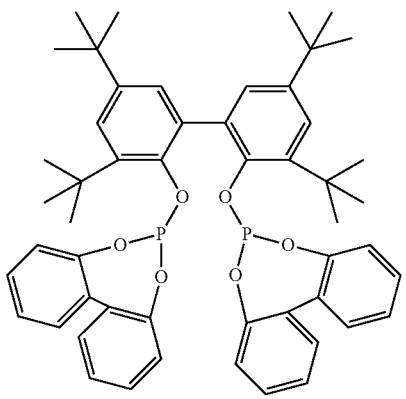

[1]

Like many organic molecules, Ligand A is a crystalline material capable of existing in a number of forms. A crystalline non-solvate and various solvate forms are disclosed in U.S. Pat. No. 8,796,481 and Yuan Hao, et al. "Crystal Structure of 6,6'-(3,3'5,5'-tetra-tertbutylbiphenyl-2,2'-diyl)Bis(oxy)didibenzo[d,f]-[1,3,2]dioxaphosphepine" *Chinese J. Struct. Chem.*, Vol 31, 673 (2012).

US 2014/0288322 A1 discloses a process for preparing a fast drying form of Ligand A via treatment with a secondary alcohol, e.g., isopropanol, at 72-75° C. for several hours. The crystal structure of the resulting material is not disclosed. U.S. Pat. No. 8,796,481 describes the means to make the non-solvate form of Ligand A as well as a number of solvates. Preparation of the crystalline non-solvate thus described also requires elevated temperatures, e.g., at least 65° C. and preferably above 85° C. While both the form of Ligand A described in US 2014/0288322 A1 and U.S. Pat. No. 8,796,481 are suitable for hydroformylation applications, elevated temperatures are required to produce them. Exposing bisphosphites to elevated temperatures may increase decomposition and thereby lower the yield of the valuable product.

Alternatively, one may choose to produce a crystalline solvate; however, adding the solvate form of a ligand into an industrial hydroformylation process would, by definition, introduce the accompanying solvent of crystallization as a contaminant. In addition, the amount of said solvent of crystallization is variable depending on the drying conditions and does not contribute to the hydroformylation reaction, i.e., the solvent acts as a diluent or filler in the solid ligand.

A third alternative would be to prepare and use a desolvated form, but effectively drying solvated materials is known to take days under forcing conditions; see US 2014/0288322 A1. Such procedures can also result in decomposition, e.g., oxidation due to extended handling, and will increase the production time and, therefore, the cost of manufacture.

Thus, it would be desirable to have a form of Ligand A that dries quickly, is thermally stable, and that can be prepared via a facile, cost-effective process that avoids prolonged exposure to elevated temperatures. Heretofore, the Ligand A crystal structure of the invention, hereinafter designated Ligand A', has not been recognized.

SUMMARY OF THE INVENTION

The invention is a crystalline form of 6,6'-[[3,3',5,5'-tetrakis(1,1-dimethylethyl)-[1,1'-biphenyl]-2,2'-diyl]bis(oxy)]bisdibenzo[d,f][1,3,2]-dioxaphosphepin, which displays its two strongest reflections, stated as 2Θ values, at 7.8±0.2° and 19.7±0.2° in an X-ray powder diffractogram, measured at 25° C. with Cu-Kα radiation.

Further aspects of the invention include: a) a method for producing a transition metal catalyst from Ligand A', wherein Ligand A' is provided and brought into contact with transition metal catalyst precursors (oxides, carbonyls, etc.) or a complex of a transition metal in an inert solvent; b) a catalyst prepared by said method; and c) a catalytic process for hydroformylation, hydrocyanation or hydrogenation, wherein the catalyst is prepared by said method.

Surprisingly, the crystalline form of the invention is low in solvent content, thermally stable, and may be prepared without exposure to high temperatures.

DETAILED DESCRIPTION OF THE INVENTION

The crystalline form Ligand A' can be prepared by a process that employs as starting materials a nonlinear alcohol and a solvate form of Ligand A.

Figure 2:
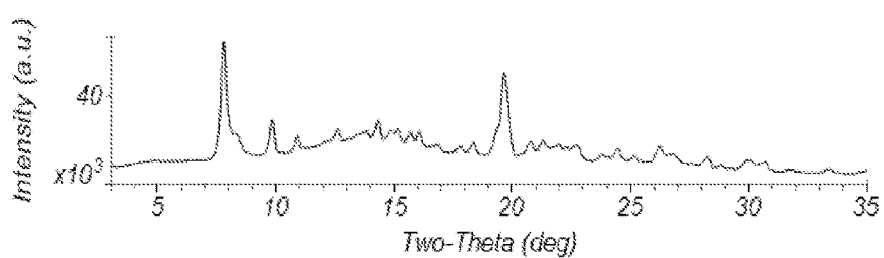
FIG. 2 is the XRD diffractogram for Ligand A' as prepared in Examples 1 and 2.

As used herein, the terms "non-solvate," "crystalline non-solvate" and "non-solvate form" are used interchangeably, and mean the crystalline form that consists of molecules of Ligand A that, when analyzed by powder XRD, will give a diffractogram similar to that shown in FIG. 2. U.S. Pat. No. 8,796,481 describes the non-solvate form of Ligand A. The crystalline non-solvate may be additionally characterized by a melting point, as determined by DSC, of about 244° C.±3° C.

As used herein, the terms "solvate," "crystalline solvate" and "solvate form" are used interchangeably, and refer to arrangements of molecules of Ligand A that include either stoichiometric or other significant amounts of solvent molecules incorporated within the crystal lattice, i.e., solvents of crystallization, such as described, for example, in "Solid State Physics" (2nd Edition), J. R. Hook, H. E. Hall, Manchester Physics Series, John Wiley & Sons (2010). Mentioning the specific solvent incorporated within the lattice is done for clarity, e.g., toluene solvate, ethyl acetate solvate, propyl acetate solvate, hexane solvate, acetone solvate, etc.

As used herein, the terms "desolvated form," and "desolvated isomorph" are used interchangeably and mean crystalline Ligand A that was originally in a solvate form, but has subsequently been dried so as to remove the solvent of crystallization.

As used herein, the term "solvent-free" means that the solvent content of Ligand A or Ligand A' is below 0.5% by weight. The weight percentage of solvent is determined by gas chromatography (GC)/mass spectrometry (MS) (decane as internal standard).

As used herein, the term "fast drying" means that the material is capable of being dried faster than the solvate form of Ligand A.

As used herein, the term "trituration" means that solids are thoroughly mixed in a solvent to form a slurry. It is noted that, although a small portion of the solids may dissolve, trituration does not include the complete dissolution of Ligand A or Ligand A', such as would occur during a recrystallization.

As used herein, the term "ppmw" means parts per million by weight.

As used herein, the term "solvent of crystallization" means solvent that is incorporated within the crystal structure.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

Solvates of Ligand A are known, and can be prepared as described, e.g., in US 2014/0288322 and U.S. Pat. No. 8,796,481. Specific examples of solvates of Ligand A include the toluene solvate, the ethyl acetate solvate, and the propyl acetate solvate. Acetate solvates are preferred starting material of the invention. Mixtures of solvates can be employed.

The nonlinear alcohols employed in the process to make the crystalline form Ligand A' are shown in Formulas 2 and 3. Noncyclic saturated, branched alcohols, such as isopropanol and its analogs, are represented by Formula 2, wherein each $R^{14}$ independently is H or a substituted or unsubstituted monovalent hydrocarbon moiety containing from 1 to 8 carbon atoms, with the proviso that at least two of $R^{14}$ are not hydrogen. Cyclic alcohols, such as cyclohexanol and its analogs, are represented by Formula 3, wherein n is 2 to 5, m is from 0 to [(2n)+5], and each $R^{15}$ is independently a substituted or unsubstituted monovalent hydrocarbon moiety. In one embodiment of the invention, m is 0 to 3. Mixtures of alcohols can be employed. The alcohol can be a tertiary or secondary alcohol, with secondary alcohols being generally preferred. In one embodiment of the invention, each $R^{14}$ or $R^{15}$ is unsubstituted.

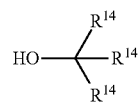

[2]

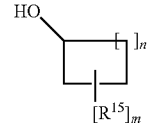

[3]

$C_3$-$C_6$ secondary alcohols, such as isopropanol, cyclohexanol, 2-butanol, 2- or 3-pentanol, and the like, are preferred. t-Butanol is the preferred tertiary alcohol. Isopropanol is the most preferred nonlinear alcohol, as it is inexpensive and readily separated from the final product Ligand A'. In one embodiment of the invention, the alcohol used is substantially peroxide-free to avoid oxidation of the ligand. As used herein, the term "substantially peroxide-free" means that the alcohol contains less than 10 ppmw peroxides.

Small amounts of amine additives, as taught in copending application serial no. PCT/US15/026648, may also be employed to mitigate excessive acid-catalyzed decomposition. The preferred amine is triethanolamine. Traces of these amines do not appear to form amine-solvates during the preparation of Ligand A'. In various embodiments of the invention, the amine is added to the slurry and/or to the alcohol. In various embodiments, the amine concentration is less than 1 wt. %, less than 0.1 wt %, or less than 0.01 wt %, based on the weight of the slurry.

The preparation process is conducted under conditions sufficient to prepare Ligand A'. In one embodiment, a solvate of Ligand A is triturated in the alcohol under conditions detailed below. The resulting slurry is then separated into a primarily solid phase and a primarily liquid phase. The primarily solid phase may be dried to obtain dry Ligand A'.

The trituration of Ligand A employs the alcohol and the solvate form of Ligand A in amounts that may be mixed effectively. The amount of nonlinear alcohol is not particularly critical, as the ligand does not dissolve to an appreciable extent, but the alcohol advantageously is employed in an amount that is sufficient to generate a slurry. The resulting slurry should be capable of being easily stirred and should provide good heat transfer, as evidenced by having a uniform temperature, and good handling, e.g., the slurry advantageously can be easily transferred to other equipment such as a filter, if desired.

Methods for preparing slurries are well known to those skilled in the art, and the slurry can be prepared by any convenient method. The slurry can be prepared using any suitable equipment including, for example, stirred vessels such as stirred tanks or reactors, stirred filters/dryers, recirculating static mixer tanks, and the like. The type of vessel is not particularly critical. In one embodiment of the invention, the equipment is capable of operating under an inert gas, e.g., $N_2$ or Ar, atmosphere in order to prevent ligand oxidation and to minimize flammability hazards. While accurate temperature control is not critical, in one embodiment of the invention, the equipment may include means to enable monitoring and controlling the temperature of the slurry.

Once formed, the slurry is treated at a combination of time and temperature sufficient to produce the novel crystal structure of Ligand A'. For instance, suitable combinations of time and temperature are given in the Examples hereinbelow. In one embodiment of the invention, good stirring of the slurry is maintained during the time and temperature treatment. In one embodiment of the invention, this treatment is done under conditions sufficient to also remove a substantial amount of any trapped, residual impurities. Examples of residual impurities include acids, chlorides, amine salts, and the like.

The Ligand A' formed in the process is recovered. In one embodiment of the invention, the liquid of the slurry is removed from the solids comprising Ligand A'. The manner of separating the solids from the bulk of the liquid of the slurry is not particularly critical. Unit operations for separating solids from liquids are well known to those skilled in the art and include, for example, sedimentation, filtration, spray drying, fluidized bed drying, centrifugation, such as in a hydrocyclone or centrifuge, and combinations thereof. Equipment for use in conducting said unit operations are also well known, and many suitable types are commercially available. In one embodiment of the invention, the recovery equipment is capable of separation of solids from liquids, preferably by filtration or centrifugation. In one embodiment of the invention, the recovered solids are a damp form of Ligand A' that primarily comprises Ligand A' with some residual liquid from the slurry. The filter cake may optionally be washed or rinsed. Such washing is advantageously done with the same alcohol employed for the trituration.

The temperature at which the solid Ligand A' is recovered is not critical and may be performed at a temperature or range of temperatures that includes ambient temperature. In one embodiment, the separation is performed at a temperature or range of temperatures that is above ambient temperature. The slurry preparation and the liquid/solid separation operations can be done in separate units, or in equipment suitable for conducting preparation, heat treatment, and separation in one piece of equipment.

In one embodiment of the invention, the damp Ligand A' is dried prior to use or storage. Unit operations for drying solids are well known to those skilled in the art. Equipment for use in drying solids is also well known, and many suitable types are commercially available, including for example, belt dryers, drum dryers, filter dryers and the like, with heating provided by convection, conduction, and radiation including, for example, infrared, microwave and radio frequency radiation, and combinations thereof. Multistage drying processes, such as flash drying followed by an agitated paddle dryer, may be employed.

Ligand A' is a crystalline form of 6,6'-[[3,3',5,5'-tetrakis (1,1-dimethylethyl)-[1,1'-biphenyl]-2,2'-diyl]bis(oxy)]bis-dibenzo[d,f][1,3,2]-dioxaphosphepin, which displays its two strongest reflections, stated as 2Θ values, at 7.8±0.2° and 19.65±0.2° in an X-ray powder diffractogram, measured at 25° C. with Cu-Kα radiation.

In one embodiment of the invention, the novel crystalline form of Ligand A' is solvent-free. An XRD of Ligand A' prepared according to Example 1 is shown in FIG. 2. FIG. 2 includes at least 5 of the reflections given in Table 1 as 2Θ values and as the interplanar spaces d:

TABLE 1

| XRD Data for Ligand A' (*represents shoulder) | | | |
|---|---|---|---|
| # | 2Θ Angle | Intensity | d (Å) |
| 1 | 7.8 ± 0.2 | S | 11.31 |
| 2 | 8.3 ± 0.2 | M* | 10.61 |
| 3 | 9.9 ± 0.2 | M | 8.96 |
| 4 | 10.9 ± 0.2 | W | 8.10 |
| 5 | 12.6 ± 0.2 | W | 7.02 |
| 6 | 13.8 ± 0.2 | W | 6.40 |
| 7 | 14.3 ± 0.2 | W | 6.18 |
| 8 | 15.1 ± 0.2 | W | 5.86 |
| 9 | 15.7 ± 0.2 | W | 5.65 |
| 10 | 16.1 ± 0.2 | W | 5.52 |
| 11 | 19.7 ± 0.2 | S | 4.51 |

Figure 1:
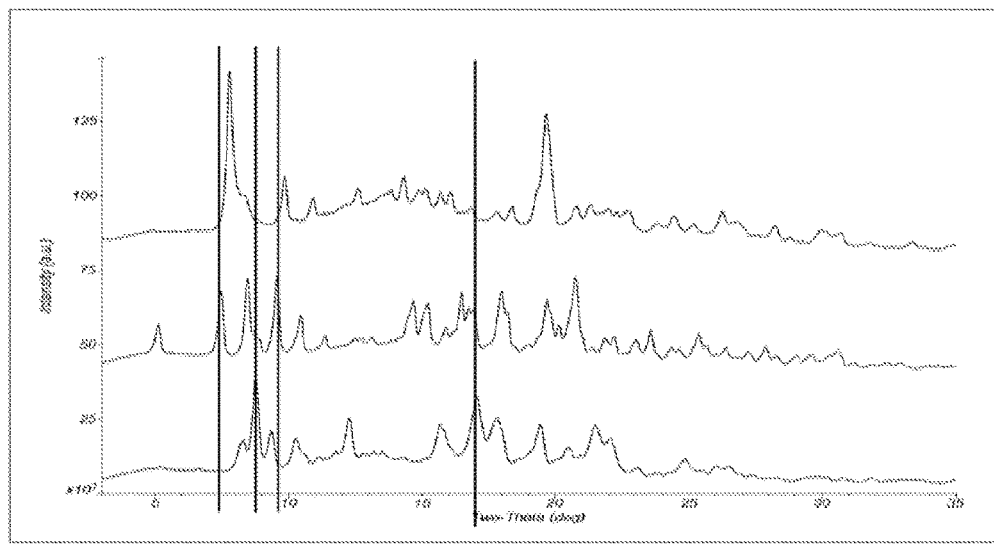
FIG. 1 is a comparison of X-ray diffraction (XRD) data for Ligand A' (top), the solvate of Ligand A (middle), and the nonsolvate of Ligand A (bottom).

It has been observed, that many of the reported forms of Ligand A have similar angles of reflection, yet the XRD diffractograms are clearly distinct. By analogy to infrared spectroscopy, the background-corrected peak intensities are judged as strong, medium or weak, wherein strong (S) is greater than 60% of the maximum intensity of the highest peak, medium (M) is 30-59%, and weak (W) is less than 29%. The diffractograms of Ligand A' and the ethyl acetate solvate and non-solvate are shown in FIG. 1. There are clearly differences in intensities that help distinguish the different crystalline forms. For example, the Ligand A' diffractogram has an unique, very intense peak at 7.8 2Θ, whereas the solvate and non-solvate diffractograms have multiple reflections, such as a pattern that roughly resembles a 1:2:2:1 quartet in the 5-10° and a triplet in the 8-10° 2Θ region, respectively. Ligand A' also has a second very intense characteristic complex peak at 19.65° 2Θ. Ligand A' lacks significant reflections, or peaks, found in other forms, such as the 2Θ peaks at 8.5° and 16.8°, for the non-solvate, and 7.3°, 9.6° and 16.8°, for the solvate. For the purposes of the invention, the term "lacking a significant reflection" means there is no reflection with a background-corrected intensity greater than 5% of the maximum intensity of the highest peak.

A second characteristic of Ligand A' is a melting point of 202-208° C., as determined by DSC, without additional phase transitions at lower temperatures.

SPECIFIC EMBODIMENTS OF THE INVENTION

All parts and percentages in the following examples are by weight unless otherwise indicated.

XRD is measured using a Bruker D8 Advance θ-θ X-ray diffractometer equipped with a copper sealed-source tube and a Vantec-1 linear position sensitive detector. The tube is operated at 35 kV and 45 mA and the samples are illuminated with copper $K_\alpha$ radiation (λ=1.541 Å). XRD data are collected with a 3° detector window from 3° to 35° 2Θ, with a step size of 0.026° and 1 s/step collection times. Analysis of the resulting X-ray diffraction patterns is performed at 25° C. using JADE2010 X-ray diffraction analysis software. Unless otherwise indicated, 2Θ values reported herein are based on Cu-Kα radiation.

DSC is performed using a TA Instruments Q2000 DSC equipped with an autosampler and a RCS-90 mechanical cooling accessory. The samples are weighed and sealed in hermetic aluminum pans and lids. The pans are sealed such that residual solvent can leave the pan during thermal cycling. The average weight is approximately 7 mg for each sample. A −85° C. to 275° C. thermal profile with a rate of 10° C./min is used. The heating scan of a sample is analyzed using Universal Analysis V4.5A software.

Thermogravimetric analysis (TGA) is performed using a TA Instruments Q500 thermogravimetric analyzer equipped with an autosampler. A nominally 10-20 mg portion of the sample is placed into a tared, homemade quartz TGA liner, which is then placed onto a platinum pan and loaded into the instrument. The sample is scanned at 10° C./min. from room temperature to 900° C. Analysis is completed using Universal Analysis 2000 V4.5A software.

Unless otherwise indicated, residual solvent is determined by dissolving Ligand A or A' in tetrahydrofuran (THF) and analyzing by GC/mass spectrometry (MS) (decane as internal standard).

Example 1

The starting material is the ethyl acetate solvate of Ligand A prepared according to the method of Example 1 of US 2014/0288322 and contains 8.25 wt % ethyl acetate. That ligand (2 g) is slurried with 30 mL of isopropanol for about 1 hour at 45° C. under N₂. The solids are filtered at 45° C., washed with 15 mL of isopropanol and dried in vacuo at room temperature overnight. The residual solvent content is below 0.5 wt %. The XRD for this material is shown in FIG. 2.

Example 2

The procedure of Ex. 1 is repeated except that the ligand is slurried at 23° C. The residual solvent content is below 0.5 wt %. The XRD for this material is the same as that shown in FIG. 2.

Figure 3:
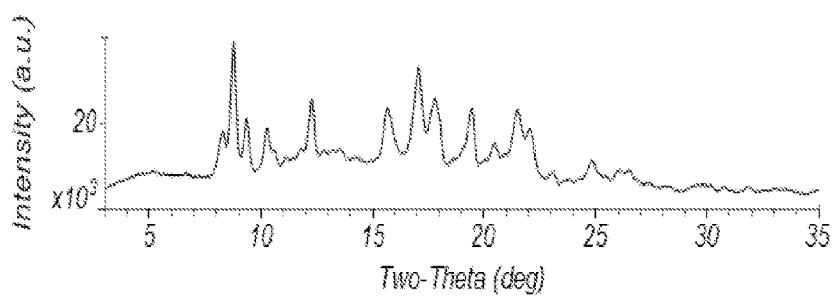
FIG. 3: is the XRD diffractogram for Ligand A as prepared in Comparative Experiment A.

Comparative Experiment A—Non-Solvate (Not an Embodiment of the Invention)
Example 1 is repeated except that the ligand is slurried at 75° C. for 3 hours. The mixture is allowed to cool to ambient temperature for about an hour. Solids are collected and dried in vacuo at ambient temperature overnight. The non-solvate is observed, as confirmed by XRD; see FIG. 3.

Figure 4:
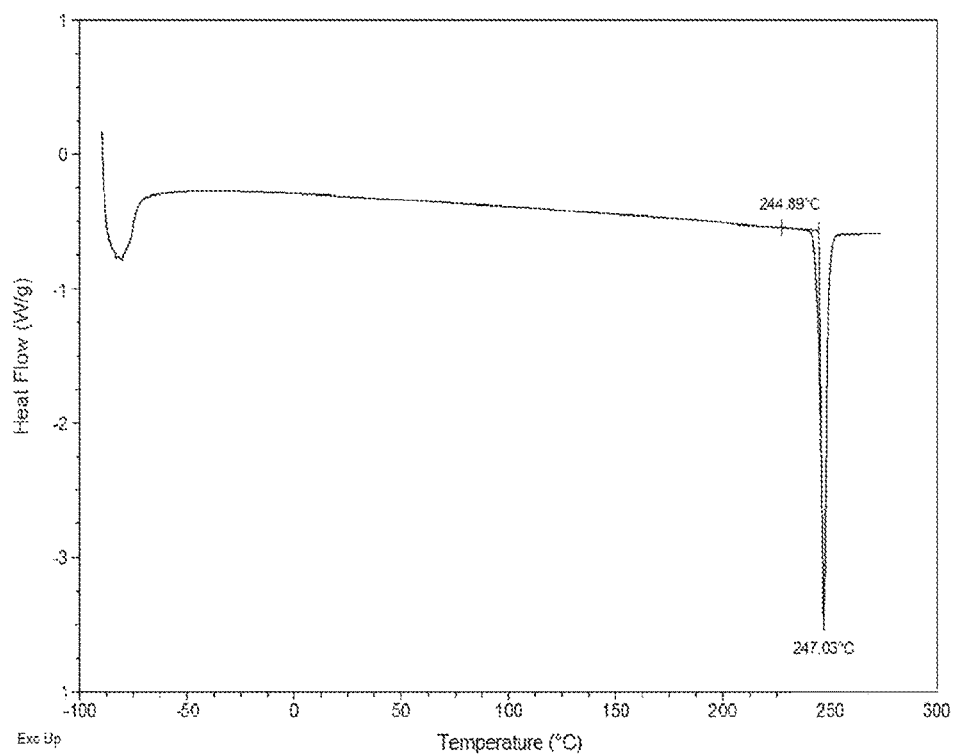
FIG. 4: is a differential scanning calorimetry (DSC) plot for the non-solvate form of Ligand A as prepared in Comparative Experiment A.

The DSC for this material is shown in FIG. 4. An endotherm, consistent with a melting event, with a peak onset of 245° C. and peak temperature of 247° C. is observed.

Example 3

Example 2 is repeated except that the slurry is stirred over the weekend. GC analysis of the residual solvent of the dried product indicates that ethyl acetate and isopropanol are below 0.5 wt %, and the XRD diffractogram is comparable to that of the product of Example 1.

Figure 5:
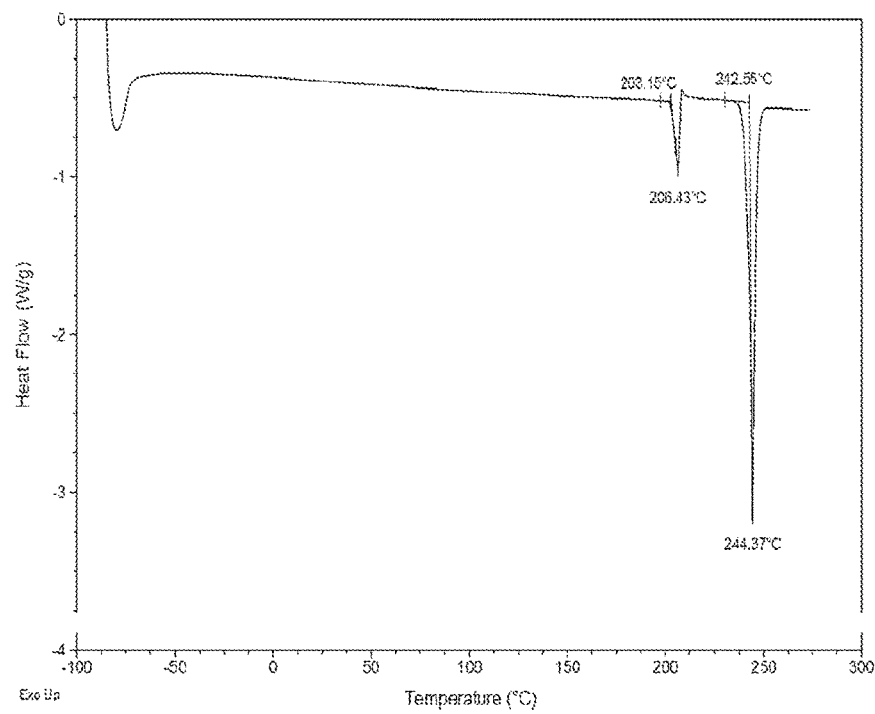
FIG. 5: is a DSC plot for Ligand A' as prepared in Example 3.

The DSC for the product of Example 3 is shown in FIG. 5. There is an initial endothermic transition with an onset temperature at 203° C. and a peak at 206° C. A second endotherm transition takes place at a peak temperature of 244° C. TGA data for this material is shown in FIG. 9B. Mass loss of less than 0.2 weight percent is observed up to the temperature range used in the DSC trace. This result indicates that no significant amount of solvent remains in the sample. The combination of the DSC and TGA results indicates that the initial endotherm represents a phase transition to the non-solvate, which then melts at around 242-244° C.

Figure 6:
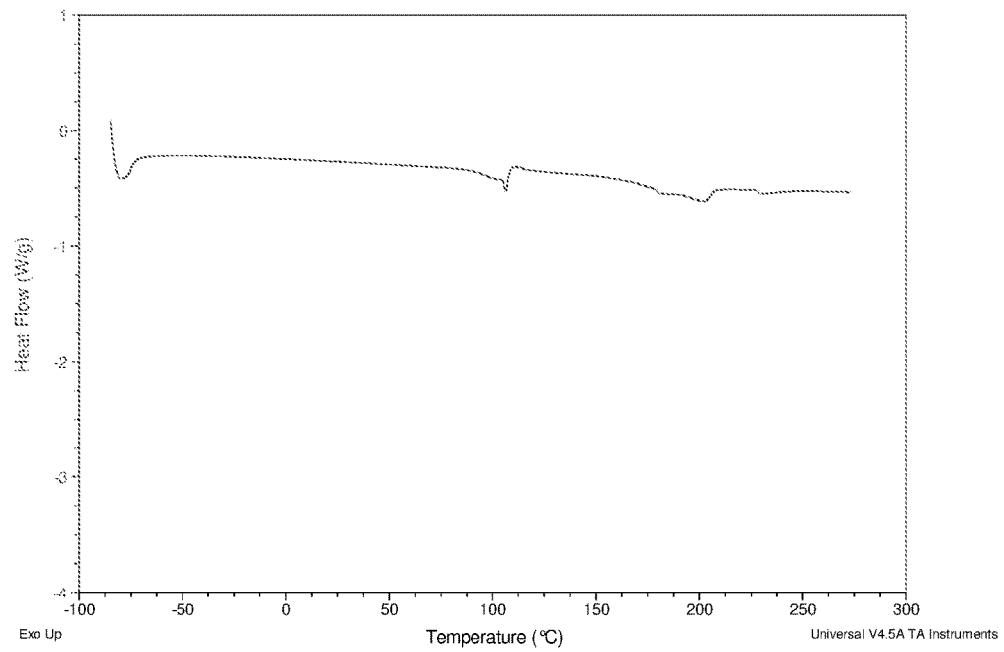
FIG. 6: is a DSC plot for the desolvated isomorph of Ligand A as prepared in Comparative Experiment B.

Comparative Experiment B—Desolvated Isomorph (Not an Embodiment of the Invention)
Ligand A (3.2 g) is dissolved in toluene (30 g) at 70° C. and then is concentrated to 45 wt. % toluene under vacuum before being slurried in isopropanol at 45° C. The resulting material is filtered but not subjected to a subsequent isopropanol rinse, and is dried. The resulting material contains 0.3% residual solvent, yet gives an XRD pattern consistent with a solvate form (e.g., identical to that of C.E. C, below, and FIG. 1 of U.S. Pat. No. 8,796,481). The lack of solvent content combined with the XRD data indicates that the material is a desolvated isomorph. This material has the relatively nondescript DSC pattern shown in FIG. 6, which pattern is similar to that observed in FIG. 2 of US 2013/0225849, and this material lacks the melting point of the non-solvate (see FIG. 4).

Figure 9:
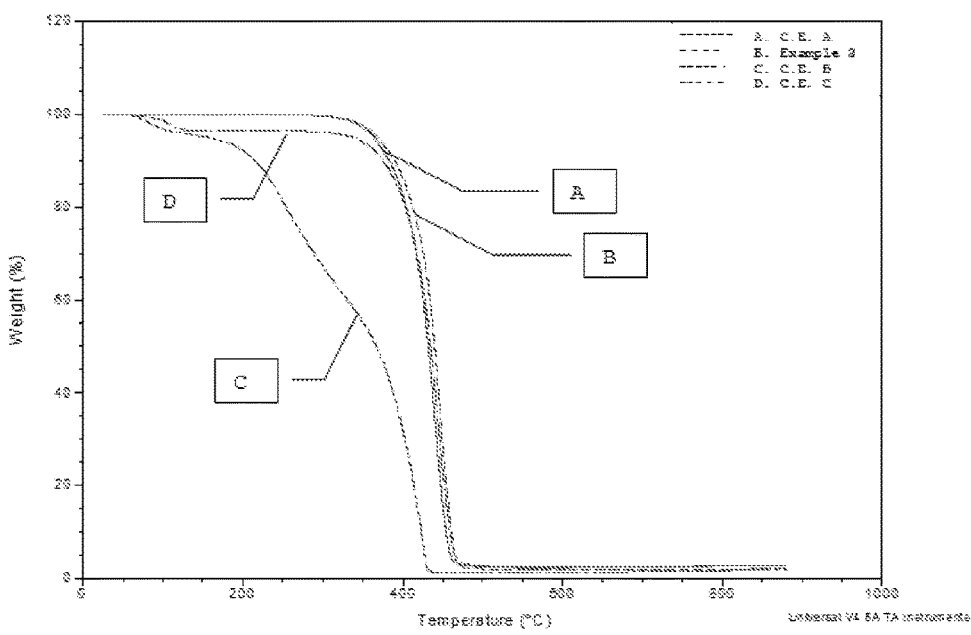
FIG. 9: is a thermogravimetric analysis (TGA) plot for materials prepared in Example 3, and Comparative Experiments A, B and C.

The TGA data for this material is shown in FIG. 9, Line C, and is clearly different than the non-solvate and Ligand A'. Significant mass loss occurs over a broad temperature range, which is indicative of substantial decomposition.

Figure 7:
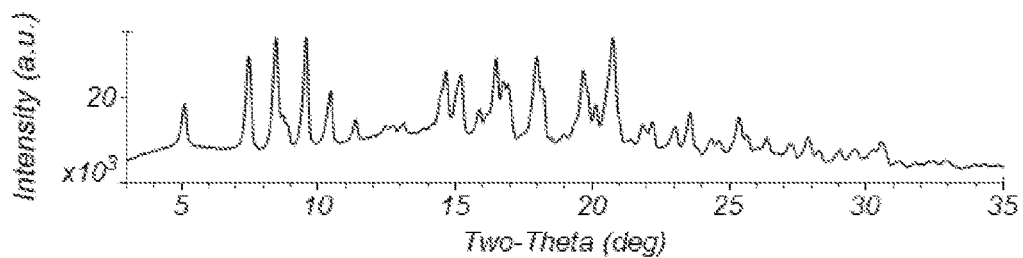
FIG. 7: is the XRD diffractogram for the ethyl acetate solvate of Ligand A as prepared in Comparative Experiment C.

Comparative Experiment C—Ethyl Acetate Solvate (Not an Embodiment of the Invention)
A solution of 15.1 g of Ligand A, prepared according to the method of Example 1 of US 2014/0288322, is dissolved in 230 mL of degassed ethyl acetate at 70° C. and then cooled to ambient temperature over several hours. The resulting ethyl acetate solvate crystals are filtered and dried in vacuo for 2 days. The resulting material exhibits the XRD diffractogram, shown in FIG. 7, of the ethyl acetate solvate.

Figure 8:
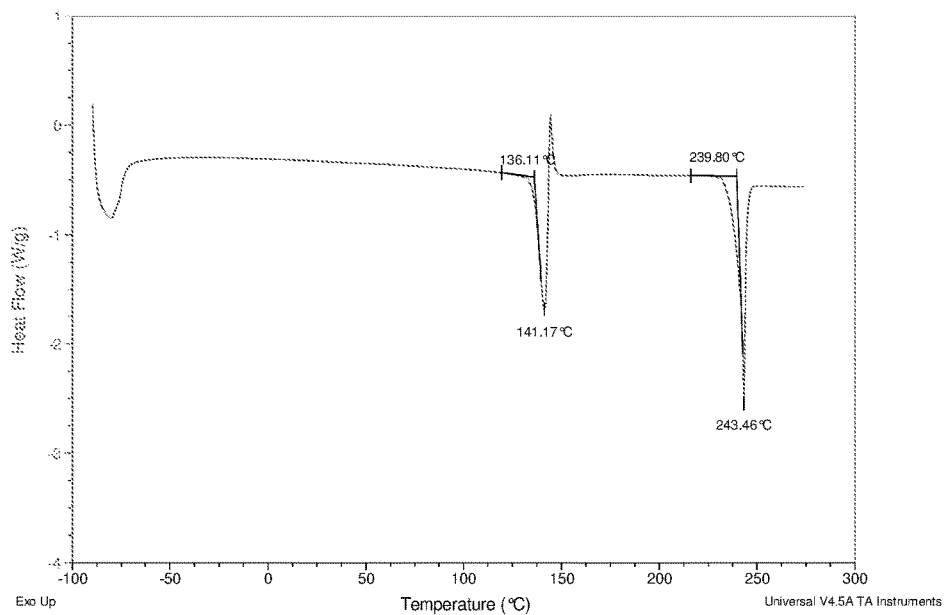
FIG. 8: is a DSC plot for the ethyl acetate solvate of Ligand A as prepared in Comparative Experiment C.

The DSC of the ethyl acetate solvate, shown in FIG. 8, exhibits an initial melting peak around 141° C. followed by a transition to the non-solvate at about 150° C. The non-solvate subsequently melts at 243° C.

The TGA data in FIG. 9 shows little loss of mass for either Ligand A' (FIG. 9; line B) or the non-solvate form (FIG. 9; line A) at temperatures up to 380° C. indicating excellent thermal stability. The solvate (FIG. 9; line D) shows an early loss of mass caused by desolvation at approximately 120° C. but no decomposition is observed below 380° C. In contrast, the desolvated isomorph (FIG. 9; line C) exhibits a continuous loss of mass that begins at relatively low temperatures (<200° C.) and continues throughout the analysis. Thus, Ligand A' and the non-solvate represent the only two forms that are both low in solvent content and thermally stable.

What is claimed is:
1. A crystalline form of 6,6'-[[3,3',5,5'-tetrakis(1,1-dimethylethyl)-[1,1'-biphenyl]-2,2'-diyl]bis(oxy)]bisdibenzo[d,f][1,3,2]-dioxaphosphepin, which displays its two strongest reflections, stated as 2Θ values, at 7.8±0.2° and 19.7±0.2° in an X-ray powder diffractogram, measured at 25° C. with Cu-Kα radiation.

2. The crystalline form of claim 1 wherein the diffractogram displays at least 3 of the following reflections:

| # | 2θ Angle (°) |
|---|---|
| 1 | 8.3 ± 0.2 |
| 2 | 9.9 ± 0.2 |
| 3 | 10.9 ± 0.2 |
| 4 | 12.6 ± 0.2 |
| 5 | 13.8 ± 0.2 |
| 6 | 14.3 ± 0.2 |
| 7 | 15.1 ± 0.2 |
| 8 | 15.7 ± 0.2 |
| 9 | 16.1 ± 0.2 |

3. The crystalline form of claim 1 that is solvent-free.

4. The crystalline form of claim 1 lacking a significant reflection at 8.5±0.2° 2θ in an X-ray powder diffractogram, measured at 25° C. with Cu-Kα radiation.

5. The crystalline form of claim 1 having a melting point of 202-208° C., as determined by DSC.

6. The crystalline form of claim 5 having a DSC plot that exhibits an initial endothermic transition with a peak at 206° C.

7. The crystalline form of claim 1 having the XRD diffractogram of FIG. 2.

8. The crystalline form of claim 1 having the TGA plot of FIG. 9 line B.

\* \* \* \* \*